United States Patent [19]

Schwan et al.

[11]  4,125,529
[45]  Nov. 14, 1978

[54] 4-ACETOXY-1,2,3,4-TETRAHYDRO-2,2-DIMETHYL-6,7-METHYLENEDIOXYISOQUINOLINIUM IODIDE

[75] Inventors: Thomas J. Schwan; Marvin M. Goldenberg, both of Norwich, N.Y.

[73] Assignee: Morton-Norwich Products, Inc., Norwich, N.Y.

[21] Appl. No.: 826,161

[22] Filed: Aug. 19, 1977

[51] Int. Cl.$^2$ .......................................... C07D 217/10
[52] U.S. Cl. ...................................... 546/90; 424/258
[58] Field of Search ................................... 260/286 Q

[56] References Cited

U.S. PATENT DOCUMENTS

| 3,853,994 | 6/1971 | Mathison et al. ..................... 260/287 |
| 4,033,966 | 7/1977 | Sawa .................................. 260/286 Q |

OTHER PUBLICATIONS

Darlak, R., and C. Muth, "Journal of Organic Chemistry", vol. 30, 1904–1909. (1965).

*Primary Examiner*—Donald G. Daus
*Assistant Examiner*—Lisa Jones
*Attorney, Agent, or Firm*—Anthony J. Franze

[57] ABSTRACT

4-Acetoxy-1,2,3,4-tetrahydro-2,2-dimethyl-6,7-methylenedioxyisoquinolinium iodide is useful as a gastric acid antisecretory agent.

1 Claim, No Drawings

4-ACETOXY-1,2,3,4-TETRAHYDRO-2,2-DIMETHYL-6,7-METHYLENEDIOXYISOQUINOLINIUM IODIDE

This invention is concerned with the compound 4-acetoxy-1,2,3,4-tetrahydro-2,2-dimethyl-6,7-methylenedioxyisoquinolinium iodide, which inhibits gastric acid output and which thus finds utility as a medicinal agent. Thus, when administered perorally to rats in a dose of 300 mg/kg, gastric acid production was inhibited by 78%.

The method currently preferred for preparing this compound is illustrated in the following example:

A.
1,2,3,4-Tetrahydro-4-hydroxy-2,2-dimethyl-6,7-methylenedioxyisoquinolinium iodide A mixture of 84 g (0.37 mole) of 4-hydroxy-6,7-methylenedioxy-1,2,3,4-tetrahydroisoquinoline hydrochloride, 102 g (0.74 mole) of potassium carbonate, 78.8 g (0.56 mole) of methyl iodide and 1000 ml methanol was refluxed for 27 hrs. The slurry was filtered while hot. The filtrate was refrigerated overnight and filtered. A light tan solid was washed with methanol and ether and dried to give 55 g (43%) of the desired product; m.p. 223°–226°.

An analytical sample, m.p. 224°–226°, was obtained by recrystallization from methanol.

Anal. Calcd. for $C_{12}H_{16}INO_3$: C, 41.28; H, 4.62; N, 4.01. Found: C, 41.33; H, 4.68; N, 3.92.

B.
4-Acetyl-1,2,3,4-tetrahydro-2,2-dimethyl-6,7-methylenedioxyisoquinolinium iodide A 26 g (0.075 mole) portion of A. was added to 200 ml of acetic anhydride and the reaction mixture was refluxed for 1.7 hrs., cooled to room temperature and filtered. The off-white solid was washed with 400 ml of ether and air dried; m.p. 249°–250° dec. Yield: 28 g (97%).

An analytical sample, m.p. 246°–248° dec., was obtained by recrystallization from 95% ethanol.

Anal. Calcd. for $C_{14}H_{18}INO_4$: C, 42.98; H, 4.64; N, 3.58. Found: C, 43.14; H, 4.54; N, 3.51.

The compound described herein exhibits a salutary effect upon gastric acid secretion. Such effect is evidenced using a modified standary pylorus-ligated secretory testing procedure in the rat. Sprague-Dawley rats, weighting 180–210 g and previously fasted for 24 hrs., were used. The compound was given perorally as a suspension in 0.5% Methocel 1 hr. prior to pylorus ligation. Under light ether anesthesia, the rat stomach was ligated at the pylorus region. Four hrs. after ligation, the conscious rat was sacrificed by a chloroform overdose. The stomach was carefully excised and its content drained into a centrifuge tube. Samples were centrifuged to separate secretions from debris. Gastric fluid volume reading and determination of sample contamination, based on debris and sample color, were made. Titration was performed on a sample aliquot of 1 ml diluted to a volume of 5 ml using distilled water. The titrant used was 0.1N NaOH. Total gastric acid output in the stomach was determined by titration to pH 7. A dose of 300 mg/kg p.o. of the compound was administered to a group of rats and its effect on the volume of gastric secretion and acid output compared to a control group receiving 0.5% Methocel p.o. At this dosage, the instant compound evoked a 78.6% inhibition of gastric acid output as well as a reduction in the volume of gastric secretions.

What is claimed is:

1. The compound 4-acetoxy-1,2,3,4-tetrahydro-2,2-dimethyl-6,7-methylenedioxyisoquinolinium iodide.

* * * * *